United States Patent [19]

Yasuda et al.

[11] 4,277,439

[45] Jul. 7, 1981

[54] GAS COMPONENT DETECTOR

[75] Inventors: Eturo Yasuda, Okazaki; Minoru Ohta, Anjo, both of Japan

[73] Assignee: Nippon Soken, Inc., Nishio, Japan

[21] Appl. No.: 86,039

[22] Filed: Oct. 18, 1979

[30] Foreign Application Priority Data

Oct. 25, 1978 [JP] Japan .................................. 53/131230

[51] Int. Cl.$^3$ ............................................ G01N 27/12
[52] U.S. Cl. ...................................... 422/94; 73/27 R; 324/71 SN; 338/22 SD; 338/34; 340/633; 422/88; 422/90; 422/98; 23/232 E
[58] Field of Search ............... 422/119, 88, 90, 94–98; 123/119 EC, 32 EE; 324/71 SN; 338/34, 22 SD; 340/633, 634; 73/27 R

[56] References Cited

U.S. PATENT DOCUMENTS

| 4,099,922 | 7/1978 | Yasuda et al. | 422/98 |
| 4,120,270 | 10/1978 | Asano | 123/119 EC |
| 4,151,503 | 4/1979 | Germak et al. | 338/22 SD |

FOREIGN PATENT DOCUMENTS 1509 4/1979 European Pat. Off. .................... 422/98

OTHER PUBLICATIONS

IC OP-AMP Cookbook, Jung 1976, pp. 514–515.

*Primary Examiner*—Michael S. Marcus
*Attorney, Agent, or Firm*—Cushman, Darby & Cushman

[57] ABSTRACT

In a gas component detector, a first gas component detecting element is formed by a metal oxide having an electric resistance depending on the concentration of gas components and on the temperature of a detected gas. A second gas component detecting element is formed by a metal oxide having the same temperature coefficient of electric resistance as that of the first gas component detecting element and having an electric resistance depending on the concentration of gas components and on the temperature of the detected gas and having a slower detection response time against the concentration of gas components in the detected gas than that of the first gas component detecting element.

10 Claims, 10 Drawing Figures

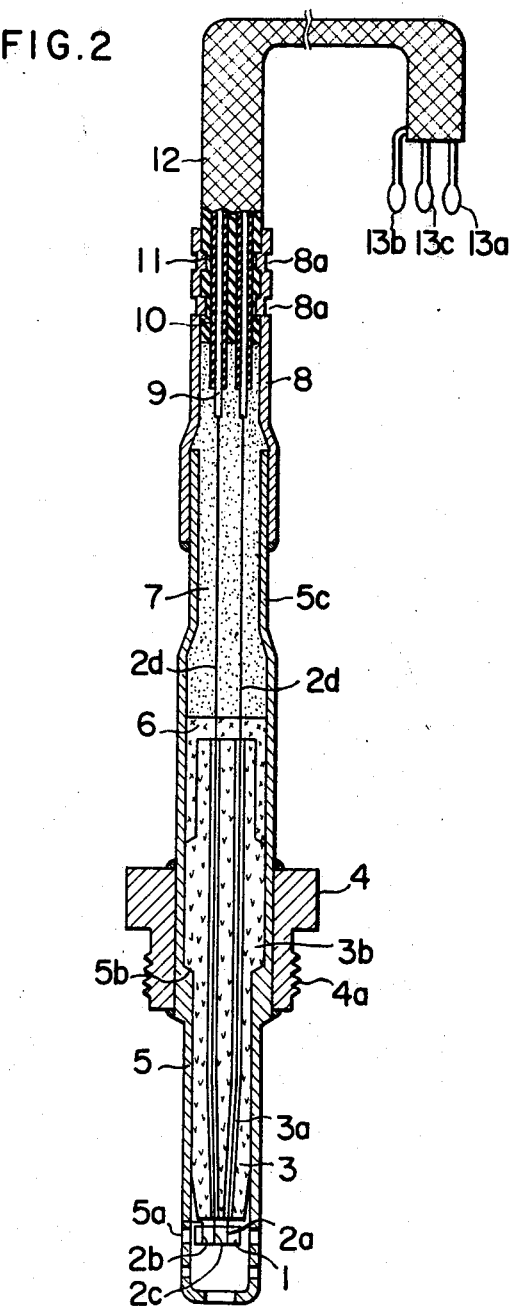

GAS COMPONENT DETECTOR

BACKGROUND OF THE INVENTION

This invention relates to a gas component detector which detects the concentration variation of gas components such as $O_2$ (oxygen), CO (carbon monoxide) and HC (hydrocarbon) in the exhaust gas of an internal combustion engine as a variation of the whole atmosphere of the engine.

According to one method for detecting the air-fuel ratio of mixture supplied to the internal combustion engine, a gas component detecting element is used, which is formed by metal oxide such as titanium oxide sensitive to the concentration of exhaust gas components and shows a value of electric resistance corresponding to the concentration of exhaust gas components. There has been an apparatus for detecting the air-fuel ratio of mixture, in which the above-mentioned gas component detecting element is connected in series with a fixed reference resistor and a variation of electric resistance value is taken from a connection point between the detecting element and the resistor to compare the resistance value with a reference voltage. However, such a prior art apparatus can not make accurate detection of an air-fuel ratio due to the following reasons. That is, when the temperature of exhaust gas varies, the electric resistance of the gas component detecting element also varies, so that even if there is no variation of exhaust gas components the voltage at the connection point between the gas component detecting element and the fixed reference resistor varies. Furthermore, the prior art apparatus is defective in that the electric resistance vs. temperature characteristic of the gas component detecting element varies with age, losing the capability of proper measurement of exhaust gas components.

SUMMARY OF THE INVENTION

The object of this invention is to solve the above-mentioned defects, which comprises a first gas component detecting element which shows an electric resistance value depending on the concentration of gas components and the temperature of the detected gas such as the exhaust gas of an internal combustion engine; and a second gas component detecting element having a similar property of electric resistance to that of the first gas component detecting element with the same temperature coefficient of electric resistance as that of the first element. However the response time of detecting the concentration of gas component is slower than that of the first element. With this simple arrangement, this invention attains an accurate detection of the concentration of gas components of the detected gas without any influence from the temperature variation of the detected gas and of the age variation of the first and second gas component detecting elements.

BRIEF DESCRIPTION OF THE DRAWINGS

Other objects, features and advantages of this invention will be readily apparent from the detailed description taken in conjunction with the accompanying drawings, in which:

FIG. 2 is a partial sectional view showing the set-up structure of the gas component detector shown in FIG. 1;

DESCRIPTION OF THE PREFERRED EMBODIMENTS

Figure 1:
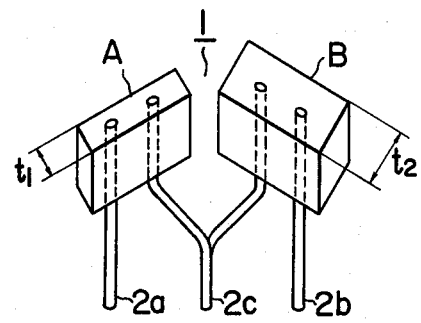
FIG. 1 is a perspective view showing a first embodiment of a gas component detector according to this invention.

Next, the invention will be explained in conjunction with embodiments shown in the drawings.

FIG. 1 is a sketch of the first embodiment of a gas component detector seen obliquely from the top, where A denotes a first gas component detecting element while B denotes a second gas component detecting element, both elements having a planar shape. The thickness $t_1$ of the first element A is smaller than $t_2$ of the second element B ($t_1 < t_2$). Both elements are formed by metal oxide such as titanium oxide ($TiO_2$), to the external surfaces and interiors of which a catalyzer, e.g. platinum, is mounted. Since the first and second gas component detecting elements A and B are made of the same material, they have the same temperature coefficient against electric resistance. Near the central portion in the direction of thickness (depth), electrodes of platinum $2a$, $2b$ and $2c$ are provided in order to measure an electric resistance corresponding to the temperature of the detected gas. The electrode $2c$ is used in common.

Next, explanation will be made of the operation of the first and second gas component detecting elements A and B which are placed in the exhaust gas of an internal combustion engine. As is well known, exhaust gas is composed of $O_2$, NOx, CO, HC and $H_2$, etc. The concentration of each component varies with the air-fuel ratio before combustion. Both elements show an electric resistance depending on the whole atmosphere rather than the variation of partial pressure of each gas component, and also depending on the temperature of exhaust gas. Since the thickness $t_1$ (e.g. $t_1 = 0.5$ mm) of the first gas component detecting element A is smaller than the thickness $t_2$ (e.g. $t_2 = 1$ mm) of the second gas component detecting element B, the first element A responds more quickly to a variation of the concentration of each gas in the exhaust gas than the second element B, that is, the electric resistance of the first element A varies more rapidly.

Next, one embodiment of the set-up structure of the above-mentioned gas component detector will be explained with reference to FIG. 2. The reference numeral 1 denotes gas component detecting elements A and B. $2a$, $2b$ and $2c$ are electrodes of platinum, etc. and $2d$ is a pair of sub-lead wires of heat resistive metal such as tungsten which are welded to the electrodes $2a$, $2b$ and 2c to be electrically connected thereto. 3 is a cylindrical ceramic body having a pair of small perforation holes 3a each having the same diameter, into which the electrodes 2a and 2b and the sub-lead wire 2d are inserted. The ceramic body 3 is formed of electrically insulating ceramic. 4 is a housing of heat resistive metal having a screw portion 4a to be mounted on an exhaust tube. 5 is a pipe having a plurality of holes at its lower end for passing therethrough exhaust gas and a step portion 5b in contact with a step portion 3b of the ceramic body 3. The pipe 5 is formed of heat resistive metal and fixed to the ceramic body tightly by the both step portions 3b and 5b and further welded air-tightly to the housing 4. 6 is a glass seal agent filled between the ceramic body 3 and the pipe 5 in order to seal the opening of the perforation hole 3a of the ceramic body 3 in a solidified state. The glass seal agent 6 ensuring the sealing of exhaust gas and the insulative fixing of the sub-lead wires 2d. 7 is powder of alumina and magnesia, etc. for fixing and electrical insulation between the sub-lead wires 2d. 8 is a pipe of heat resistive metal welded to the pipe 5. 9 denotes a pair of lead wires electrically connected to the sub-lead wires 2d by welding. The outer portion of the lead wires is covered with a cover 10 of heat-proof electrically insulating material such as glass wool and heat resistive gum, etc. The cover 10 is further covered with another cover 11 with the same material such that the lead wires 9 are electrically insulated from each other. 12 is a cover formed of heat resistive metal braiding covering the outer portion of the cover 11 and fixed to the pipe 8 by calking the end portion 8a of the pipe 8. The end portion of the pipe 5 is calked as shown by 5c in order to enhance the filling density of the electric insulating powder. The electrode 2b is welded to the pipe 5 which is connected electrically to the pipe 8 and the braiding 12 and taken out of a terminal 13b. The electrodes 2a and 2c conduct through the sub-lead wire 2d and the lead wire 9 which are taken out of terminals 13a and 13c, respectively.

Figure 3:
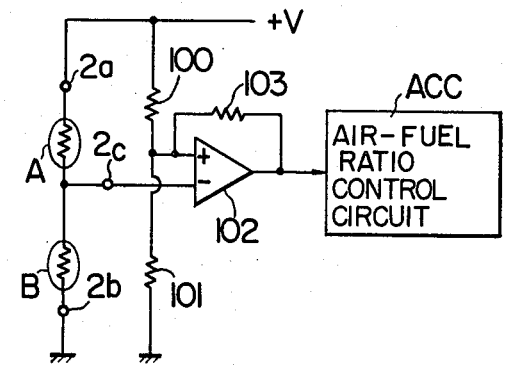
FIGS. 3 and 5 are electric circuit diagrams showing detection circuits of the gas component detector shown in FIG. 1.
Figure 4:
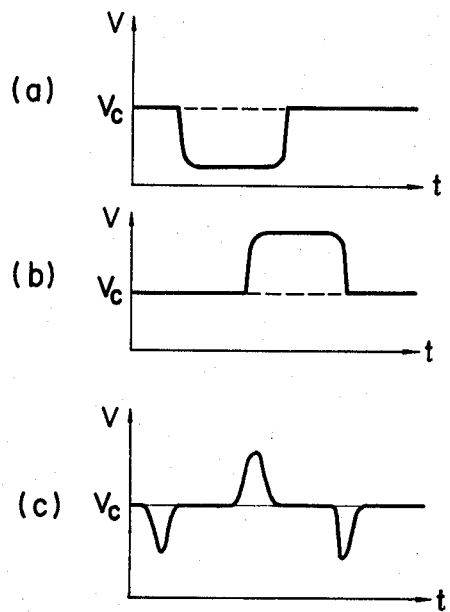
FIG. 4 shows waveforms for the explanation of the operation of the detection circuit of FIG. 3.

Next, explanation will be made of the operation and the construction of a detecting circuit which derives a signal from the first and second gas component detecting elements A and B in accordance with the concentration of each gas component. The gas component detector is connected to a voltage supply +V, as shown in FIG. 3. When the detector is placed in the exhaust gas of an internal combustion engine, a voltage signal depending on the concentration of exhaust gas components is obtained from the electrode 2c. When the air-fuel ratio of the mixture varies from a value larger than a theoretical one (hereinafter called a rich state) to a value smaller than the theoretical value (hereinafter called as lean state), the time required for the variation of the resistance of the second gas component detecting element B (i.e. detection response time) is longer than the time required for that of the resistance of the first gas component detecting element B, the resistance value of the first element A precedingly increases and after the lapse of a predetermined time the second element B varies. As a result, the voltage of the electrode 2c of FIG. 3 falls and then rises toward an initial level, as shown in FIG. 4a. On the other hand, if the air-fuel ratio varies from the lean state to the rich state, the resistance of the first gas component detecting element A drops first and thereafter, at a constant interval, the resistance of the second gas component detecting element B drops. As a result, the voltage at the electrode 2c rises and then falls toward the initial level, as shown in FIG. 4b. In FIG. 4, the ordinate is voltage (V) while the abcissa is time (t), and Vc denotes a voltage without variation of the concentration of the exhaust gas components. FIG. 4c shows the voltage variation of the electrode 2c when the rich and lean states are repeated. Flat portions between plus and minus peaks corresponds to the response lag time of the engine. Even if the temperature of the exhaust gas varies, the resistances of the first and second gas component detecting elements A and B are varied by the same value. So, the voltage at the electrode 2c is scarcely influenced by temperature. Since both the first and second gas component detecting elements A and B are formed by the same material, the voltage at the electrode 2c has only an extremely small influence of variation over age. The electrode 2c is connected to the inverted input terminal of a comparator 102, while the non-inverted input terminal is connected to a connection point between resistors 100 and 101 to which a comparison reference voltage Vc is given. The resistor 103 gives hysteresis to the comparator 102. The digital signal of either "0" or "1" level from the output of the comparator 102 is applied to an air-fuel ratio control circuit ACC to be used as an air-fuel ratio control signal. The detecting circuit gives a "0" level signal to the air-fuel ratio control circuit ACC when the voltage of the electrode 2c becomes higher than the reference voltage Vc (i.e. when the lean state changes to the rich state), in order to correct the air-fuel ratio from the lean to the rich state. On the contrary, when the voltage of the electrode 2c is lower than the reference voltage Vc (i.e. when the rich state changes to the lean state), the detecting circuit gives a "1" level signal to the air-fuel ratio control circuit in order to correct the air-fuel ratio from the rich state to the lean state.

Figure 5:
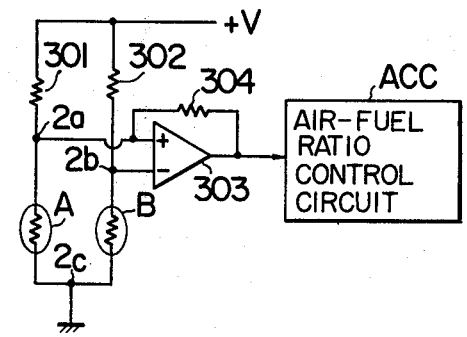
Figure 6:
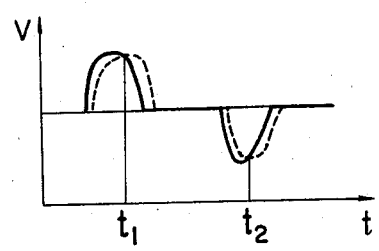
FIG. 6 shows waveforms for the explanation of the operation of the detection circuit of FIG. 5.

FIG. 5 shows another embodiment of a detecting circuit, in which the electrode 2c of the gas component detector is grounded. The electrode 2a at the connection point between a first gas component detecting element A and a resistor 301 is connected to a non-inverted input terminal of a comparator 303 and the electrode 2b at the connection point between a second gas component detecting element B and a resistor 302 is connected to the inverted input terminal of the comparator 303. In the case of using the set-up structure as shown in FIG. 2, the terminal 2b is to be substituted by the terminal 2c. The resistor 304 inhibits both input terminals of the comparator 303 from becoming the same voltage and the output signal from becoming unstable. The output signal of the comparator 303 is applied to the air-fuel control circuit ACC which is used as an air-fuel control signal. The operation of this detecting circuit will be explained hereinafter with reference to FIG. 6 showing the voltage waveforms of the electrodes 2a and 2b of FIG. 5 by solid and broken curves respectively. Flat portions between positive and negative peaks correspond to the response lag time of the engine. Since the detection response time of the second gas component detecting element B against the concentration of the exhaust gas components is slower than that of the first gas component detecting element A, the waveform of the broken curve shifts from the waveform of solid curve by a constant time. At the time $t_1$ when the air-fuel ratio of the mixture gas is smaller than the theoretical value (rich state), the voltage of the electrode 2a becomes smaller than that of the electrode 2b. Hence, the output signal of the comparator 303 inverts from the "1" level to the "0" level. This signal is applied to the air-fuel ratio control circuit in order to correct the air-fuel ratio from the rich state to the lean state. At the time $t_2$ when the air-fuel ratio is in the lean state, the voltage of the electrode $2a$ becomes larger than that of the electrode $2b$. Hence, the output signal of the comparator 303 inverts from the "0" level to the "1" level. The signal is applied also to the air-fuel ratio control circuit in order to correct the air-fuel ratio from the lean state to the rich state. Furthermore, even if the temperature of the exhaust gas varies, the resistances of the first and second gas component detecting elements A and B vary in the same way. So, the difference in the voltages of electrodes $2a$ and $2b$ is hardly influenced by temperature. Since both elements A and B are formed of the same material, the voltage difference between the electrode $2a$ and $2b$ suffers little from age variation.

Figure 7:
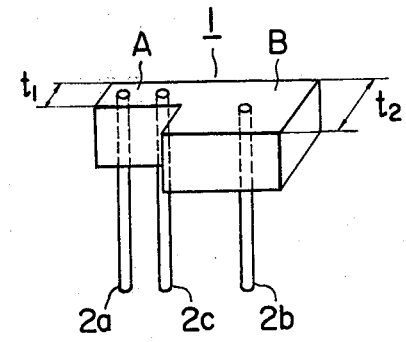
FIG. 7 is a perspective view showing a second embodiment of a gas component detector according to this invention.

Next, explanation will be made of the second embodiment of this invention. FIG. 7 is a perspective view of a gas component detector according to the second embodiment of this invention. As in the first embodiment of FIG. 1, A is a first gas component detecting element with a thickness $t_1$, while B is a second gas component detecting element with a thickness of $t_2$ ($t_2 > t_1$). Both elements A and B are formed in one united body. Electrodes $2a$, $2b$ and $2c$ are provided near the central portions in the direction of thickness (depth). Especially, the electrode $2c$ is placed near the boundary between the first and second gas component detecting elements A and B, with one terminal used in common. The material, the surface treatment, the operation in the exhaust gas, and the setting-up structure, etc. of this gas component detector are the same as those of the gas component detector of the first embodiment. The detecting circuit to which the gas component detector is connected is also the same as that of the first embodiment. So, further explanation of them is omitted.

Figure 8:
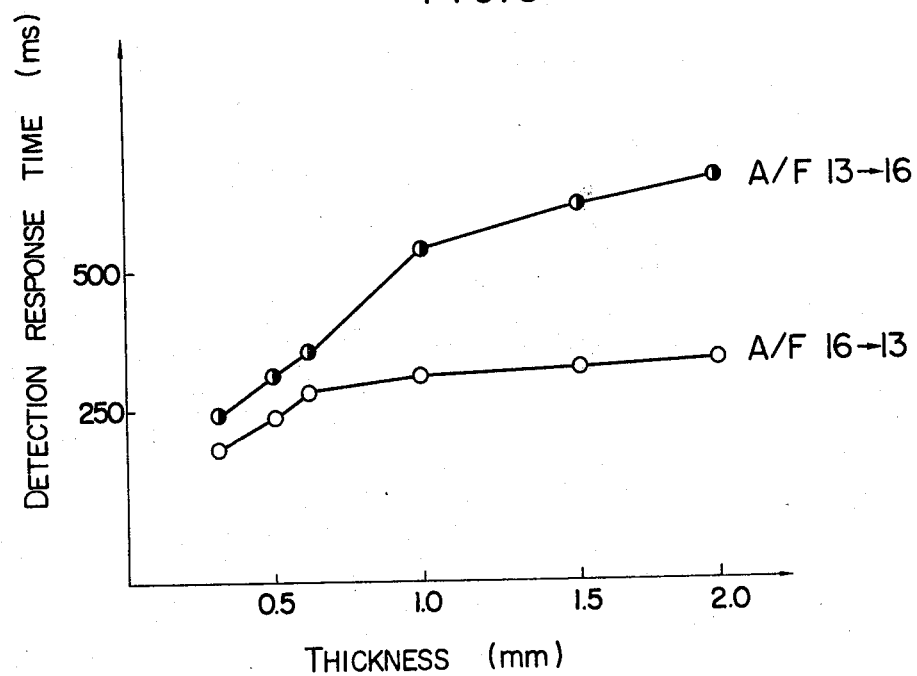
FIG. 8 shows a characteristic diagram for the explanation of the operation of the gas component detector according to first and second embodiments.

FIG. 8 shows a relationship between the thickness (mm) of the first and second gas component detecting elements A and B and the detection response time (ms) at which a variation appears in the resistance as the concentration of the exhaust gas component varies. Cases in which the air-fuel ratio (A/F) varies from 13 to 16 and from 16 to 13 are demonstrated. For example, when the air-fuel ratio (A/F) varies from 16 to 13, the response time with thickness of 0.5 mm is 230 msec. However, with thickness of 1 mm the response time becomes about 300 msec having a difference of 70 msec. Since the first and second gas component detecting elements A and B carry a catalyzer in order to promote reaction between gas components in the exhaust gas near the surface, an abrupt change of electric resistance happens at the value of theoretical air-fuel ratio.

Figure 9:
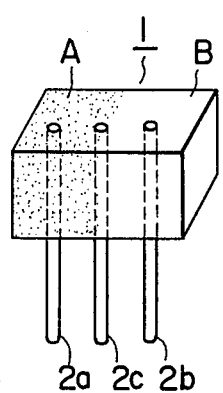
FIG. 9 is a perspective view showing a third embodiment of a gas component detector according to this invention.
Figure 10:
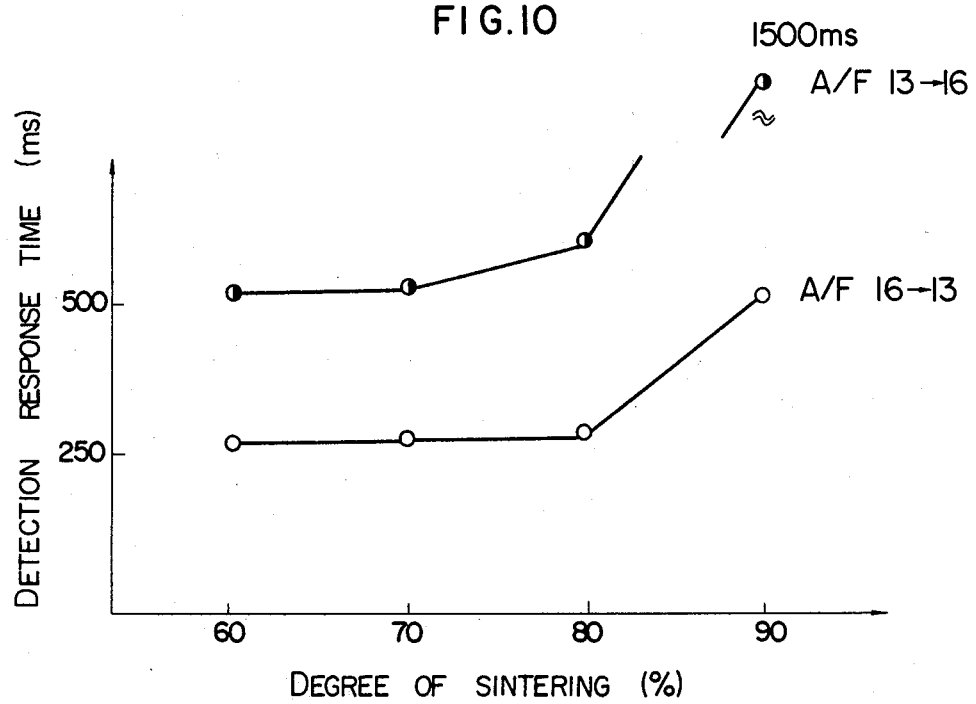
FIG. 10 shows a characteristic diagram for explanation of the gas component detector shown in FIG. 9.

Next, explanation will be made of a third embodiment of this invention, FIG. 9 is a perspective view of a gas component detector according to the third embodiment of this invention. A denotes a first gas component detecting element while B denotes a second gas component detecting element, both of which are elaborately sintered. The first and second gas component elements A and B are further formed by metal oxide such as titanium oxide ($TiO_2$), etc., on the outer and inner surfaces of which a catalyzer, e.g. platinum, is mounted. At the position near the central portion in the direction of thickness (depth) where an electric resistance related to the concentration of the gas components and the temperature of the exhaust gas can be detected, electrodes $2a$, $2b$ and $2c$ formed by platinum, etc. are provided. The electrode $2c$ used in common is mounted near the boundary between the first and second gas component detecting elements A and B. Since the first gas component detecting element A is sintered to be sufficiently porous, the exhaust gas can easily penetrate into the element to quicken the response time against the variation of concentration of the components in the exhaust gas. On the other hand, since the second gas component detecting element B is sintered tightly, it is difficult for the exhaust gas to penetrate into the element so that the response time against the variation of concentration of the components in the exhaust gas is slower than that of the first element A. FIG. 10 shows a relationship between the sintering degree (%) and the detection response time (ms). Accordingly as the sintering degree is larger, the detection response time becomes slower due to the compact structure. For example, when the air-fuel ratio (A/F) varies from 16 to 13, the detection response time for the sintering degree of 70% is 280 msec, while 520 msec for 90%, resulting in a difference of 240 msec. The operation of this gas component detector placed in the exhaust gas of an internal combustion engine, the set-up structure, and the detecting circuit to which this gas component detector is connected are the same as those of the first and second embodiments. So, explanation of them will be omitted. Although in the third embodiment the first and second gas component elements A and B are formed in a united body, they may be formed separately.

Furthermore, although in the above-mentioned embodiments the gas component detecting elements A and B are made of the same material, they may be formed by different materials the electric resistances of which vary in the same manner with temperature variation.

Although the detection response times of the gas component detecting elements A and B are discriminated either by changing the thickness or by changing the sintering degree through formation of porous or compact structure, both thickness and sintering degree may be varied for this purpose.

Finally, as for the detection circuit, it may be possible to use two comparators in the circuit of FIG. 3 and set two different comparison reference voltages in order to determine the air-fuel ratio.

What is claimed is:

1. A gas component detector comprising a first gas component detecting element formed by a metal oxide having an electric resistance depending on the concentration of gas components and on the temperature of a detected gas and having a relatively fast response time in response to the variation of concentration of gas components; a second gas component detecting element formed by a metal oxide having the same temperature co-efficient of electric resistance as that of said first gas component detecting element and having an electric resistance variable to the same extent as that of said first detecting element depending on the concentration of gas components and on the temperature of the detected gas and having a slower detection response time against the concentration of gas components in the detected gas than that of said first gas component detecting element; electrodes provided in said first and second gas component detecting elements at positions capable of detecting an electric resistance depending on the concentration of gas components and on the temperature of the detected gas; and a catalyzer carried on said first and second detecting elements whereby a value of electric resistance corresponding to the concentration of gas components and the temperature of the detected gas is derived.

2. A gas component detector according to claim 1, in which said first gas component detecting element has a porous structure while said second gas component detecting element has a compact structure.

3. A gas component detector according to claim 1 in which said first and second gas component detecting elements are integrally formed.

4. A gas component detector according to claim 1 which further comprises a comparator having a non-inverting terminal and an inverting terminal and a feedback resistor connected between the non-inverting terminal and an output thereof for providing a hysteresis operation, the non-inverting terminal being further connected to a reference potential point and the inverting terminal being connected to a connection point of said first and second gas component detecting elements.

5. A gas component detector according to claim 1 which further comprises a comparator having a non-inverting terminal and an inverting terminal and a feedback resistor connected between the non-inverting terminal and an output thereof for providing a hysteresis operation, the non-inverting terminal being further connected to said first gas component detecting element and the inverting terminal being connected to said second gas component detecting element.

6. A gas component detector comprising a first gas component detecting element formed by a metal oxide having an electric resistance depending on the concentration of gas components and on the temperature of a detected gas; a second gas component detecting element formed by a metal oxide having the same temperature coefficient of electric resistance as that of said first gas component detecting element and having an electric resistance depending on the concentration of gas components and on the temperature of the detected gas and having a slower detection response time against the concentration of gas components in the detected gas than that of said first gas component detecting element, the thickness of said second gas component detecting element being made larger than that of said first gas component detecting element; electrodes provided in said first and second gas component detecting elements at positions capable of detecting an electric resistance depending on the concentration of gas components and on the temperature of the detected gas; and a catalyzer carried on said first and second gas component detecting elements whereby a value of electric resistance corresponding to the concentration of gas components and the temperature of the detected gas is derived.

7. A gas component detector according to claim 6 in which said first and second gas component detecting elements are integrally formed.

8. A gas component detector according to claim 6 which further comprises a comparator having a non-inverting terminal and an inverting terminal and a feedback resistor connected between the non-inverting terminal and an output terminal thereof for providing a hysteresis operation, the non-inverting terminal being further connected to a reference potential point and the inverting terminal being connected to a connection point of said first and second gas component detecting elements.

9. A gas component detector according to claim 6 which further comprises a comparator having a non-inverting terminal and an inverting terminal and a feedback resistor connected between the non-inverting terminal and an output terminal thereof for providing a hysteresis operation, the non-inverting terminal being further connected to said first gas component detecting element and the inverting terminal being connected to said second gas component detecting element.

10. A gas component detector comprising a first gas component detecting element formed by a metal oxide having an electric resistance depending on the concentration of gas components and on the temperature of a detected gas; a second gas component detecting element formed by a metal oxide having the same temperature coefficient of electric resistance as that of said first gas component detecting element and having an electric resistance variable to the same extent as that of said first detecting element depending on the concentration of gas components and on the temperature of the detected gas and having a slower detection response time against the concentration of gas components in the detected gas than that of said first gas component detecting element, said first and second detecting elements being series-connected with each other; comparator means for comparing the potential at the connection point of said first and second detecting elements and a reference voltage applied thereto, in which the reference voltage is provided with hysteresis characteristic; electrodes provided in said first and second gas component detecting elements at positions capable of detecting an electric resistance depending on the concentration of gas components and on the temperature of the detected gas; and a catalyzer carried on said first and second gas component detecting elements whereby a value of electric resistance corresponding to the concentration of gas components and the temperature of the detected gas is derived.

* * * * *